United States Patent
Hoctor et al.

(10) Patent No.: US 6,898,460 B2
(45) Date of Patent: May 24, 2005

(54) METHOD AND APPARATUS FOR UTERINE CONTRACTION MONITORING USING LINEAR PREDICTIVE MODELING OF ABDOMINAL SURFACE EMG SIGNALS

(75) Inventors: Ralph Thomas Hoctor, Saratoga Springs, NY (US); Khalil John Maalouf, Clifton Park, NY (US); Yibin Zheng, Charlottesville, VA (US)

(73) Assignee: General Electric Company, Niskayuna, NY (US)

( * ) Notice: Subject to any disclaimer, the term of this patent is extended or adjusted under 35 U.S.C. 154(b) by 564 days.

(21) Appl. No.: 10/045,706

(22) Filed: Jan. 15, 2002

(65) Prior Publication Data

US 2003/0135130 A1 Jul. 17, 2003

(51) Int. Cl.[7] ................................. A61B 5/04
(52) U.S. Cl. ......................................... 600/546
(58) Field of Search ............................... 600/382, 546, 600/588; 607/138

(56) References Cited

U.S. PATENT DOCUMENTS 5,776,073 A  *  7/1998  Garfield et al. ............. 600/546
6,678,551 B2  *  1/2004  Maalouf et al. ............. 600/546

OTHER PUBLICATIONS

*Adaptive Signal Processing*, Bernard Widrow, Samuel D. Sterns, Chapter 8, Other Adaptive Algorithms and Structures, 1985 by Prentice–Hall, Inc., pp. 173–182.

* cited by examiner

*Primary Examiner*—Jeffrey R. Jastrzab
*Assistant Examiner*—Frances P. Oropeza
(74) *Attorney, Agent, or Firm*—Jean K. Testa; Christian G. Cabou

(57) ABSTRACT

A system and a method are provided for processing electromyogram (EMG) input signals from an abdominal surface to detect uterine contractions. The system comprises a sensor configured to detect a uterine EMG signal and generate an EMG input signal. The system further includes a signal processor coupled to the sensor and configured to generate an EMG prediction error signal. The signal processor performs signal-processing operations on the EMG input signal to generate the EMG prediction error signal, where the EMG prediction error signal corresponds to the magnitude of at least one contraction event and the periodicity of multiple contraction events.

26 Claims, 2 Drawing Sheets

METHOD AND APPARATUS FOR UTERINE CONTRACTION MONITORING USING LINEAR PREDICTIVE MODELING OF ABDOMINAL SURFACE EMG SIGNALS

BACKGROUND

The present invention relates generally to monitoring the medical condition of a woman in labor and in particular to processing abdominal surface electromyogram (EMG) signal data for the purpose of uterine contraction monitoring.

The present technology for monitoring uterine contraction is a tocodynamometer, which measures the abdominal pressure exerted on a belt placed around the lower abdomen of a patient in labor. However, the tocodynamometer can be uncomfortable for some patients to wear. Additionally, abdominal pressure changes can be harder to detect on larger women. Enhanced uterine contraction monitoring is required to provide obstetricians with an improved tool to diagnose whether a patient is at risk of preterm labor. Because premature birth is the leading cause (85%) of infant death, improved EMG technology holds the potential to advance prenatal care and management.

It has been well established that uterine contractions are caused by electrical potentials generated and propagated by muscle cells. These electrical activities occur in bursts and give rise to measurable electric fields called electromyographic (EMG) signals. The frequency and duration of certain features of the EMG signals correspond to the frequency and duration of the uterine contractions. The temporal and spectral characteristics of an EMG signal, recorded by external electrodes, make it possible to discriminate between efficient and inefficient contractions in terms of electrical command capability. It is also reported that the spectral density of the EMG signals shifts significantly at different stages during gestation, providing a means of separating non-laboring contractions from laboring contractions. It is possible to record uterine electrical activity as early as a gestational age of 19 weeks. Therefore, an abdominal EMG signal can be of value for pregnancy monitoring.

It is known that the EMG signal can be reliably recorded by placing electrodes on the internal uterine surface. However, such a procedure is both invasive and not accepted in clinical use. It has been proposed that the EMG signals should be acquired on the exterior surface of the abdomen, and this procedure has been shown to work in practice. EMG signals acquired from the exterior surface of the abdomen can be used to detect and monitor contractions, due to the relationship between the onset of contraction and the spectral characteristics of the EMG signal. The main obstacles to such a use of EMG technology are, first, patient motion which causes noise and signal artifacts, second, interference from other physiological electrical events (such as Electrocardiogram (ECG)), and, third, imperfect electrode contacts.

There is a need for an effective means of accurately processing the EMG signal from the electrodes attached on the external abdominal wall, in order to extract from it an indication of when the periods of contraction occur.

BRIEF DESCRIPTION (EMG) signals from an external abdominal surface to detect uterine contractions. The system comprises at least one sensor configured to detect EMG signals and configured to generate a corresponding EMG input signal. The system further includes a signal processor coupled to the at least one sensor and configured to generate a corresponding EMG prediction signal. The processor performs signal-processing operations on the EMG input signal to generate the EMG prediction error signal, where the EMG prediction error signal corresponds to the magnitude of at least one contraction event and the periodicity of multiple contraction events. The EMG input signal is used in combination with a second EMG input signal to reduce noise in EMG signals.

A method is provided for processing electromyogram (EMG) signals from an abdominal surface to detect uterine contractions. The method comprises detecting an EMG signal and generating an EMG input signal. The method further includes generating an EMG prediction error signal, which corresponds to the magnitude of at least one contraction event and the periodicity of multiple contraction events.

DRAWINGS

These and other features, aspects, and advantages of the present invention will become better understood when the following detailed description is read with reference to the accompanying drawings in which like characters represent like parts throughout the drawings, wherein.

DESCRIPTION

Figure 1:
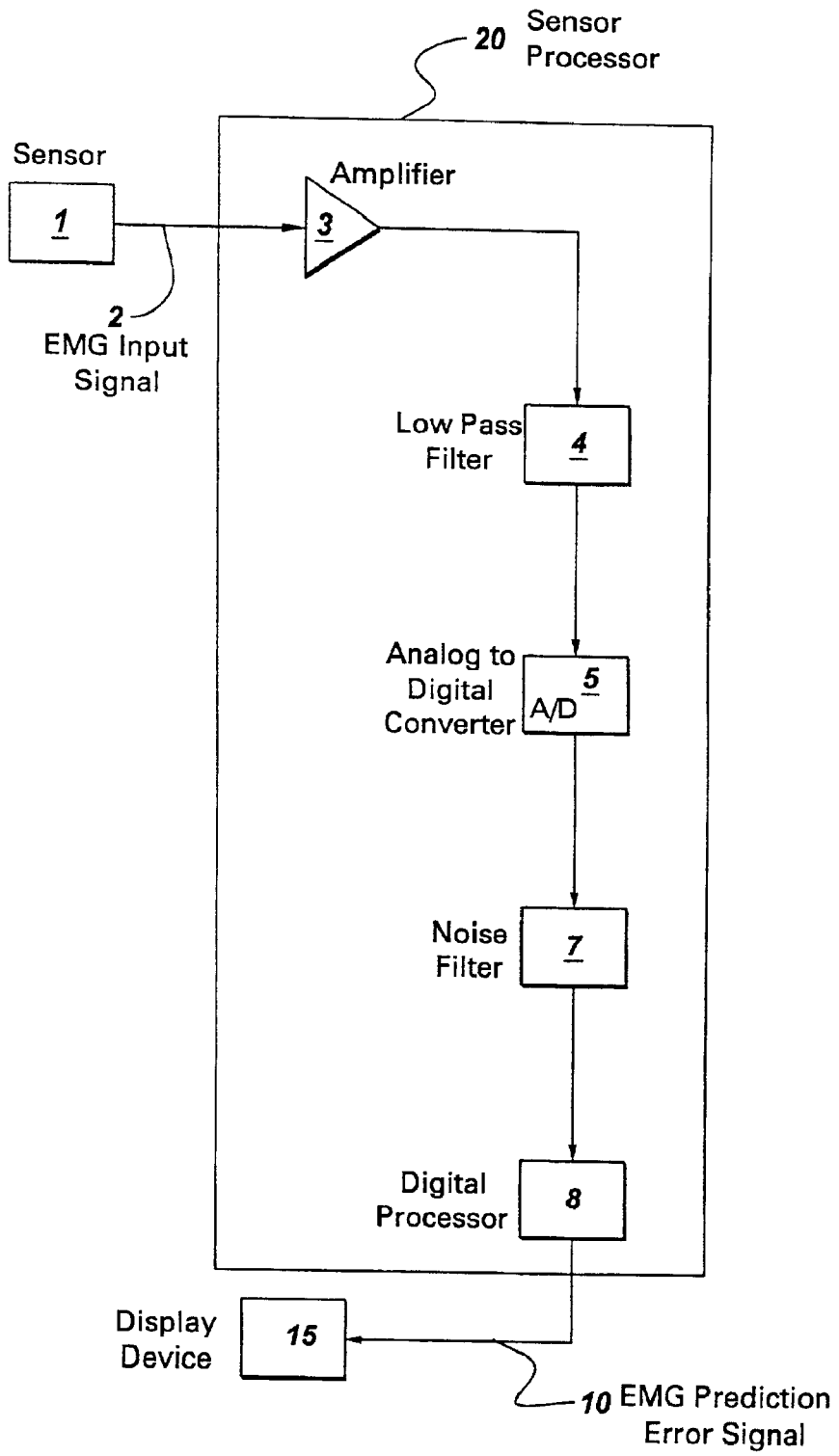
FIG. 1 is an overall block diagram representing a Uterine Contraction Monitoring System in accordance with one embodiment of the present invention.

Although the physiology of uterine EMG generation is understood to a large degree, modeling the EMG waveform based on the underlying physiological process has proven to be difficult. The EMG input signal demonstrates the characteristics of a non-stationary random process; therefore, a phenomenological approach is employed, according to which the uterine EMG signal is modeled as an auto-regressive (AR) random process as follows:

$$e[n]=x[n]+a_1 x[n-1]+ \ldots +a_p x[n-p] \quad (1)$$

Here 1) $e[n]$ represents an EMG prediction error signal, 2) $x[n]$ represents a digitized EMG input signal, 3) a computed quantity $a_1 x[n-1]+ \ldots +a_p x[n-p]$ represents an EMG prediction signal and 4) $a_1, \ldots, a_p$ represent a plurality of prediction coefficients.

The construction of AR models is well known in the signal processing art (see, for example, S. L. Marple, Jr., *Digital Spectral Analysis with Applications*, Prentice-Hall, 1987). The general AR model of (1) is applied to a specific input signal by identifying a set of prediction coefficients. These prediction coefficients are generally chosen to optimize some characteristic of the EMG prediction error signal, $e[n]$. A common approach is to choose $a_1, \ldots, a_p$ to minimize the energy in $e[n]$. Application of an AR model is equivalent to the assumption that the input signal ($x[n]$) is a colored noise random process that has been produced by filtering a white noise process with an all-pole filter.

The prediction error signal given by (1) is also known as the forward prediction error, since it is the error in predicting an observation based on past observations of the signal and thus a prediction whose sense is forward in time. It is also common to define a backward prediction error as follows:

$$e_b[n] = x[n-p] + a_1^* x[n-p+1] + \ldots + a_p^* x[n] \quad (2)$$

Here, in general, the prediction coefficients $a^*_1, \ldots, a^*_p$ are the complex conjugates of the prediction coefficients in (1). Many other common modeling techniques optimize some combination of the forward and backward prediction errors.

The approach of the present invention is also called a linear prediction model because the present value of the EMG input signal (x[n]) is "predicted" by a combination of the past values of the input signal. During the uterine contraction event the EMG input signal (x[n]) exhibits non-stationary characteristics in that the frequency content of the signal changes with time. The prediction coefficients, $a_1, \ldots, a_p$, are computed by processing a segment of contiguous data in the digitized EMG input signal (x[n]). Since any such segment represents a fixed time interval, both the prediction coefficients ($a_1, \ldots, a_p$) and the EMG prediction signal ($a_1 x[n-1] + \ldots + a_p x[n-p]$) are functions of time. The degree to which the digitized EMG input signal (x[n]) and the EMG prediction signal fail to agree will be indicated by the amplitude of the EMG prediction error signal, e[n]. The EMG prediction error signal e[n] may also be interpreted as indicating to what extent the AR modeling assumption is valid; when the EMG prediction error signal is large, the implication is that the EMG input signal is not well-modeled by a p-th order AR random process.

At the onset of the uterine contraction, the EMG input signal (x[n]) exhibits a change in spectral characteristics. The spectral characteristic change in the EMG input signal (x[n]) changes the degree to which the p-th order AR model is applicable to the EMG input signal (x[n]), which results in a change in the amplitude of the EMG prediction error signal (e[n]). The change in the amplitude of the EMG prediction error signal (e[n]) is used, in one embodiment of the present invention, to indicate uterine contraction. Conversely, at the conclusion of the uterine contraction the EMG prediction error signal returns to its former level. The change in amplitude of the EMG prediction error signal (e[n]), indicative of the change in the spectral characteristics of the EMG input signal (x[n]), can provide an indication of both the onset and conclusion of the uterine contraction.

A Uterine Contraction Monitoring System for use in detecting uterine contractions includes an (meaning at least one) sensor 1 of FIG. 1. The sensor 1 generates a corresponding EMG input signal (x[n]) 2. The sensor 1 is coupled to a signal processor 20, where the signal processor 20 generates the respective EMG prediction error signal (e[n]) 10, which represents a magnitude of at least one contraction event and periodicity of a set of multiple contraction events. The signal processor 20 is optionally coupled to a display device 15. Sensor 1 typically comprises a pair of Electrocardiogram (EKG) electrodes, for example. The signals from the EKG electrodes are recorded differentially; and the difference of two EKG electrode outputs is the output of sensor 1, which is the EMG input signal (x[n]) 2. The application of utilizing two EKG electrodes as a sensor 1 is known to one skilled in the art, and the EKG electrodes are widely available.

In one embodiment of the present invention, the signal processor 20 typically further comprises the following components to generate the EMG prediction error signal (e[n]) 10. An amplifier 3 generates an amplified representation of the EMG input signal (x[n]) 2. The amplifier 3 is coupled to a low pass filter 4. The low pass filter 4 performs anti-aliasing filtering of the amplified representation of the EMG input signal (x[n]) 2 to generate a low-pass filtered representation of the EMG input signal 2. The low pass filter 4 is coupled to an analog-to-digital converter 5. The analog-to-digital converter 5 generates a digitized representation of the EMG input signal 2, at a typical sampling frequency range from about 100 Hz to about 200 Hz, from the low-pass filtered representation of the EMG input signal (x[n]) 2. The analog-to-digital converter 5 is coupled to a noise filter 7. The noise filter 7 removes the power line structure (i.e. typically 50 Hz or 60 Hz) from the digitized representation of the EMG input signal (x[n]) 2 to produce a noise-filtered version of the EMG input signal (x[n]) 2. The noise filter 7 is coupled to a digital processor 8. The digital processor 8 can be any form of digital processing device, including, by way of example and not limitation, a standard microprocessor, a digital signal processor, or a programmable logic device. The digital processor 8 comprises an adaptation algorithm to process the noise-filtered version of the EMG input signal (x[n]) 2 and to compute the EMG prediction error signal (e[n]) 10. The digital processor 8 is optionally coupled to a display device 15. The display device 15 is identified by way of example and not limitation as a computer monitor, instrument display monitor, a bedside display monitor, printer, or a strip chart recorder. The display device 15 receives the EMG prediction error signal (e[n]) 10, such that the patient or medical practitioner can monitor and optionally record both the onset and the recession of uterine contractions.

In one embodiment of the present invention (not shown in FIG. 1), more than one sensor 1 is utilized to generate a corresponding more than one EMG input signal (x[n]) 2. An example, provided for illustration and not limitation, is where 2 sensors 1 are arranged to generate both a first EMG input signal (x[n]) 2 that corresponds to the first sensor 1 and a second EMG input signal (x[n]) 2 that corresponds to the second sensor 1. In this embodiment, the signal processor 20 processes both the first EMG input signal (x[n]) 2 and the second EMG input signal (x[n]) 2 to generate a first EMG prediction error signal (e[n]) 10 corresponding to the first EMG input signal (x[n]) 2 and a second EMG prediction error signal (e[n]) 10 corresponding to the second EMG input signal (x[n]) 2. The signal processor 20 determines whether the first or the second EMG prediction error signal (e[n]) 10 has more amplitude variation and then provides the EMG prediction error signal (e[n]) 10 with more amplitude variation to the display device 15.

In one embodiment of the present invention, the adaptation algorithm comprises an parameter estimation portion coupled with a finite-impulse-response digital filter, called a prediction error filter, to compute the EMG prediction error signal (e[n]) 10. The parameter estimation portion computes at least one prediction coefficient ($a_1, \ldots, a_p$). The parameter estimation portion of the adaptation algorithm computes the prediction coefficients ($a_1, \ldots, a_p$) in the linear prediction filter to optimize an EMG prediction error performance index, such as the long-term average of the squares of the EMG prediction error signal (e[n]) 10. The adaptation algorithm in the digital processor 8 filters the noise-filtered version of the EMG input signal (x[n]) 2 to obtain the EMG prediction error signal (e[n]) 10. If desired, the parameter estimation portion in any of a number of standard AR models produces the EMG prediction error signal (e[n]) 10 as a by-product and thereby obviates the need for the prediction error filter.

In the present invention, the use of standard AR models is acceptable. In particular, Recursive Least Squares (RLS)

and Burg adaptation algorithms are cited as adaptation algorithms that can be used in the present invention. The Recursive Least Squares and Burg adaptation algorithms are presented by way of example and not limitation, and the present invention is by no means limited to the use of these methods.

When any parameter estimation portion is utilized in the digital processor 8, the prediction error filter has a number of prediction error filter coefficients, known as the model order, which must be specified. The inventors have determined, through experimentation, that model orders in the range from 2 to 10 produce the desired indication of uterine contraction in the EMG prediction error signal (e[n]) 10. If the model order is too large, the sensitivity of the EMG prediction error signal (e[n]) 10 to the uterine contraction is reduced.

In an alternative embodiment of the present invention, the RLS method is used to compute the EMG prediction error signal 10. The RLS method is one of a class of AR modeling procedures that are referred to as sequential because, for every new data sample, a new AR model is computed. Given a model order, (p), the RLS algorithm produces a least-squares estimate of the parameters by minimizing an exponentially weighted sum of forward prediction errors. As used in the present invention, the $n^{th}$ oldest forward prediction error is weighted by the factor $w^n$. The least-squares estimate of the parameters is updated recursively, as described in many standard reference works, such as S. L. Marple, Jr. *Digital Spectral Analysis with Applications*, Prentice-Hall, 1987, chapter 9. One of the parameters for which a recursive estimate exists is the forward prediction error, which is the required output of the digital processor 8 (signal processor 20). The weight parameter, (w) in the RLS filter, is typically set so that $w^{\tilde{N}}=0.01$ for a value of N, where N is equal to the number of samples in the typical time interval in a range of from about 2 seconds to about 12 seconds.

The RLS algorithm is known to be susceptible to errors caused by the accumulation of round off or other numerical errors in the recursive computations. Various schemes have been described in the signal processing literature to address this problem.

In another embodiment, digital processor 8 utilizes a block data optimization algorithm, such as the well-known Burg algorithm. Block data methods use all of the data in a fixed data block or window to compute a single AR model. The Burg method, in particular, minimizes the sum of the squares of the forward and backward prediction errors over a given data block for a given model order, and produces, as a computational by-product, the value of that sum. The inventors have determined, through experimentation, that the model orders associated with the block data optimization algorithm method typically range from 2 to 10 to produce the desired indication of uterine contraction in the EMG prediction error signal (e[n]) 10. In the present invention, the data blocks are overlapping segments of the EMG input signal (x[n]) 2, all having the same fixed number of samples, and the output of the Burg algorithm is the computed value of the sum of squared errors. Each Burg algorithm output value is computed from the most recent data block accumulated, and the output values may be produced at the same sample rate as the EMG input signal (x[n]) 2, or at a reduced sample rate, by varying the number of new data points added to the saved data block before the next computation is performed. When a block data optimization algorithm is utilized in the digital processor 8, typical data collection window duration is from about 2 seconds to about 10 seconds.

Figure 2:
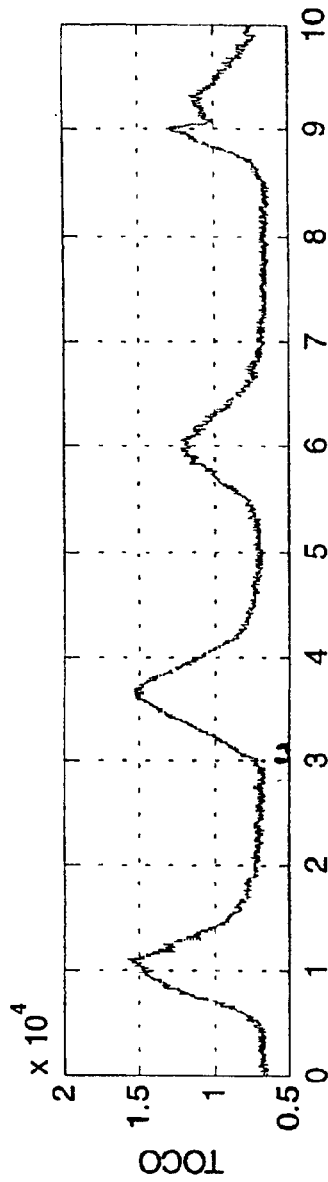
FIG. 2, is a graphic representation of responses of a tocodynamometer to a set of uterine contraction events.
Figure 3:
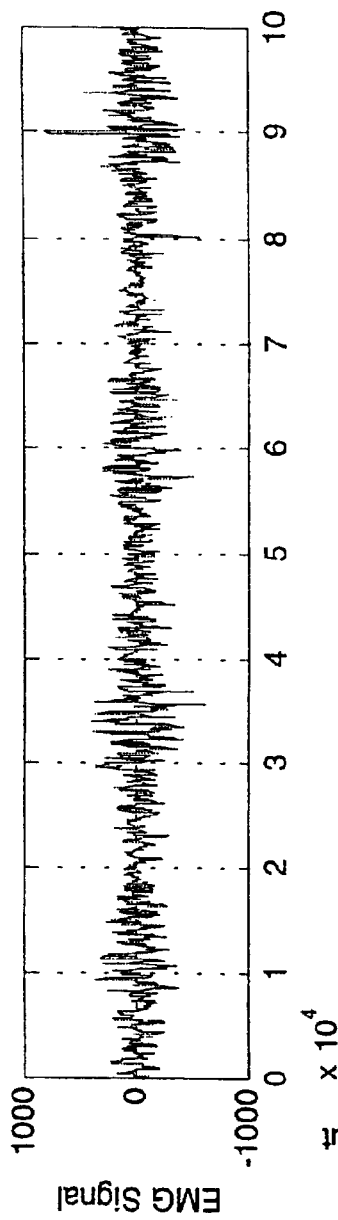
FIG. 3 is a graphic representation of the responses of a digital representation of EMG input signal to a set of uterine contraction events.
Figure 4:
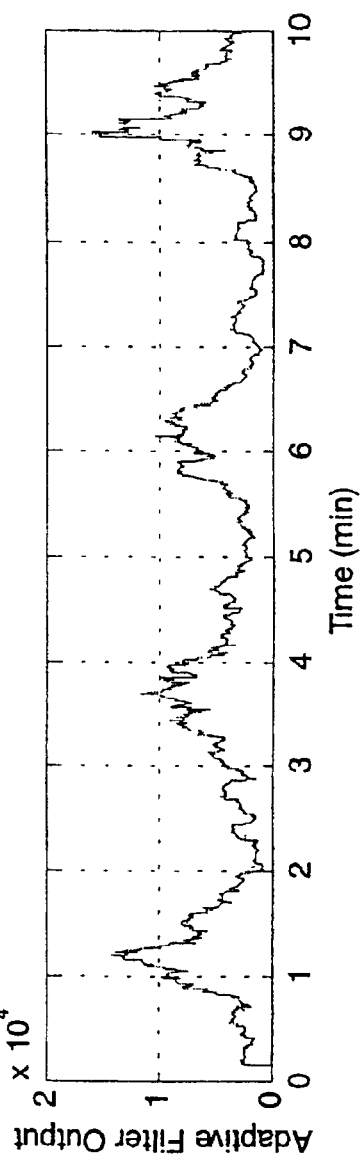
FIG. 4 is a graphic representation of responses of a digital processor output signal (EMG prediction error signal) to a set of uterine contraction events.

As an example of the processing just described, responses of a tocodynamometer, the digitized representation of the EMG input signal (x[n]) 2, and the digital processor output signal (EMG prediction error signal (e[n]) 10) to a set of uterine contraction events are provided in FIGS. 2, 3 and 4, respectively. The digital processor output signal (EMG prediction error signal (e[n]) 10) was computed using an embodiment of the present invention where the prediction error filter in the Burg algorithm is of a second order and the Burg algorithm data collection window duration was 10 seconds.

Another embodiment of the present invention utilizes a Burg algorithm with a data collection window duration of about 5 seconds, the prediction error filter of fourth order, representing a fourth order model, and the digitized representation of the EMG input signal 2 with a sampling frequency rate of about 200 Hz.

Another embodiment of the present invention utilizes a Burg algorithm with a data collection window duration of about 10 seconds, the prediction error filter of fourth order, representing a fourth order model, and the digitized representation of the EMG input signal 2 with a sampling frequency rate of about 100 Hz.

A specific embodiment of a method and apparatus for processing external abdominal surface EMG signal data for the purpose of detecting uterine contractions according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A system for processing electromyogram (EMG) input signals from an external abdominal surface to detect uterine contractions, said system comprising:

a sensor configured to detect an EMG signal and to generate a corresponding EMG input signal; and a signal processor coupled to said sensor and configured to generate a respective EMG prediction error signal, which represents a magnitude of at least one contraction event and periodicity of a set of multiple contraction events.

2. The system of claim 1 further comprising a display device coupled to said signal processor.

3. The system of claim 2, wherein said display device is selected from the group consisting of a computer monitor, a instrument display monitor, a bedside display monitor, a printer, and a strip chart recorder.

4. The system of claim 1, wherein the sensor comprises two EKG electrodes configured to be placed in contact with said exterior abdominal surface adjacent to a uterus.

5. The system of claim 1, wherein said signal processor further comprises:

an amplifier coupled to the sensor and adapted to amplify said EMG input signal and provide an amplified representation of said EMG input signal;

a low pass filter coupled to said amplifier and configured to filter said amplified representation of said EMG input signal to generate a low-pass filtered representation of said EMG input signal;

an analog to digital convener coupled to said low pass filter and configured to process said low-pass filtered representation of said EMG input signal to generate a digitized representation of said EMG input signal;

a noise filter coupled to said analog to digital converter and configured to remove a power line structure from said digitized representation of said EMG input signal to generate a noise-filtered version of said EMG input signal; and a digital processor coupled to said noise filter and configured to process said noise-filtered version of the EMG input signal to compute said EMG prediction error signal.

6. The system of claim 5, wherein said digital processor comprises an adaptation algorithm, wherein said adaptation algorithm comprises a parameter estimating portion that is configured to be coupled to a prediction error filter, wherein said parameter estimating portion is configured to compute said at least one prediction coefficient to optimize an EMG prediction error signal performance index.

7. The system of claim 6, wherein said adaptation algorithm is further configured to filter said digitized representation of said EMG input signal to compute said EMG prediction signal.

8. The system of claim 6, wherein said adaptation algorithm is selected from the group consisting of a Least Square adaptation algorithm and a Burg adaptation algorithm.

9. The system of claim 6, wherein said prediction error filter is configured to have model order in a range from 2 to 10.

10. The system of claim 6, wherein said adaptation algorithm is a Least Square adaptation algorithm that has a time interval range from about 2 seconds to about 12 seconds.

11. The system of claim 6, wherein said adaptation algorithm is a Burg adaptation algorithm that has a data collection window duration from about 2 seconds to about 10 seconds.

12. The system of claim 6, wherein said adaptation algorithm is a Burg adaptation algorithm that has a data collection window duration of about 10 seconds and said prediction error filter is of a fourth order.

13. The system of claim 12, wherein said digitized representation of said EMG input signal has a sampling frequency rate range from about 100 Hz to about 200 Hz.

14. The system of claim 6, wherein said adaptation algorithm comprises a Burg adaptation algorithm having a data collection window duration of about 5 seconds, said prediction error filter is a fourth order filter, and said digitized representation of said EMG input signal has a sampling frequency rate of about 200 Hz.

15. The system of claim 6, wherein said adaptation algorithm is a Burg adaptation algorithm having a data collection window duration of about 10 seconds, said prediction error filter is of a second order, and said digitized representation of said EMG input signal has a sampling frequency rate of about 100 Hz.

16. A method for processing electromyogram (EMG) input signals from an external abdominal surface to detect uterine contractions, said method comprises:

generating at least one EMG input signal; and computing an EMG prediction error signal which represents a magnitude of at least one contraction event and periodicity of a set of multiple contraction events.

17. The method of claim 16, further comprising displaying said EMG prediction error signal on a display device.

18. The method of claim 16, wherein said step of computing said EMG prediction error signal further comprises:

computing at least one prediction coefficient to optimize an EMG prediction error signal performance index in a parameter estimating portion of an adaptation algorithm; and filtering a digitized representation of said at least one EMG input signal in a prediction error filter of said adaptation algorithm.

19. The method of claim 18, wherein said adaptation algorithm is selected from the group consisting of a Least Square adaptation algorithm and a Burg adaptation algorithm.

20. The method of claim 18, wherein said prediction error filter has model orders in a range from 2 to 10.

21. The method of claim 18, wherein said adaptation algorithm is a Least Square adaptation algorithm that has a time interval range from about 2 seconds to about 12 seconds.

22. The method of claim 18, wherein said adaptation algorithm is a Burg adaptation algorithm having a data collection window duration from about 2 seconds to about 10 seconds.

23. The method of claim 18, wherein said adaptation algorithm is a Burg adaptation algorithm that has a data collection window duration of about 10 seconds and said prediction error filter is of a fourth order.

24. The method of claim 23, wherein said digitized representation of said EMG input signal has a sampling frequency rate range from about 100 Hz to about 200 Hz.

25. The method of claim 18, wherein said adaptation algorithm is a Burg adaptation algorithm that has a data collection window duration of about 5 seconds, said prediction error filter is of a fourth order and said digitized representation of said EMG input signal has a sampling frequency rate of about 200 Hz.

26. The system of claim 18, wherein said adaptation algorithm is a Burg adaptation algorithm that has a data collection window duration of about 10 seconds, said prediction error filter is of a second order and said digitized representation of said EMG input signal has a sampling frequency rate of about 100 Hz.

* * * * *